(12) United States Patent
Bucholtz

(10) Patent No.: US 6,471,710 B1
(45) Date of Patent: Oct. 29, 2002

(54) PROBE POSITION SENSING SYSTEM AND METHOD OF EMPLOYMENT OF SAME

(75) Inventor: Frank Bucholtz, Crofton, MD (US)

(73) Assignee: Advanced Sensor Technology, LLC, Crofton, MD (US)

( * ) Notice: Subject to any disclaimer, the term of this patent is extended or adjusted under 35 U.S.C. 154(b) by 0 days.

(21) Appl. No.: 09/635,803

(22) Filed: Aug. 11, 2000

Related U.S. Application Data

(63) Continuation-in-part of application No. 09/373,539, filed on Aug. 13, 1999.

(51) Int. Cl.[7] ............................................. A61B 19/00
(52) U.S. Cl. ...................... 606/130; 600/229; 600/230
(58) Field of Search ............................... 600/201, 188, 600/199, 229, 126, 230, 174; 248/278.1, 288.51, 316.4; 606/69, 130

(56) References Cited

U.S. PATENT DOCUMENTS

| | | | |
|---|---|---|---|
| 1,460,697 A | * 7/1923 | Bendlin | 600/126 |
| 3,631,737 A | * 1/1972 | Wells | 600/126 |
| 3,858,578 A | * 1/1975 | Milo | 600/126 |
| 3,982,474 A | 9/1976 | Klund | |
| 4,445,501 A | 5/1984 | Bersler | |
| 4,517,963 A | * 5/1985 | Michel | 600/229 |
| 4,622,644 A | 11/1986 | Hansen | |
| 4,633,079 A | 12/1986 | Rieger | 250/227 |
| 4,806,012 A | 2/1989 | Meltz et al. | |
| 4,849,962 A | 7/1989 | Blood | |
| 4,880,971 A | 11/1989 | Danisch | 250/227 |
| 4,950,883 A | 8/1990 | Glenn | |
| 4,996,419 A | 2/1991 | Morey | 250/227.18 |
| 5,007,705 A | 4/1991 | Morey et al. | 350/96.29 |
| 5,126,558 A | 6/1992 | Rogers, Jr. et al. | |
| 5,208,877 A | 5/1993 | Murphy et al. | 385/12 |
| 5,225,375 A | 7/1993 | Aite et al. | 437/225 |
| 5,260,566 A | 11/1993 | Reed | 250/227.16 |

(List continued on next page.)

FOREIGN PATENT DOCUMENTS

| | | | |
|---|---|---|---|
| EP | 0702780 B1 | 10/1997 | ........... G01B/11/16 |
| WO | WO 9424534 | 10/1994 | ........... G01L/1/24 |
| WO | WO 9429671 | 12/1994 | ........... G01B/11/18 |
| WO | WO 98/08050 | 2/1998 | |
| WO | WO 9841815 | 9/1998 | ........... G01B/21/04 |
| WO | WO 99/32862 | 7/1999 | |

OTHER PUBLICATIONS

R. Kashap "Photosensitive Optical Fibres: Devices and Applications", Optical Fibre Technol. vol. 1, pp. 17–34 (1994).

M.G. Xu, J.–L. Archambault, L. Reekie and J.P. Dakin, "Thermally–compensated Bending Gauge Using Surface– Mounted Fibre Gratings, Int. Journal of Optoelectronics", vol. 3, pp. 281–283 (1994).

C.D. Butter and G.E. Hocker, "Fibre Optics Strain Gauge, Appl. Opt." vol. 17, pp. 2876–2869 (1978).

Optical Waveguide Theory, A.W. Snyder and J.D. Love, Chapman & Hall, London, p. 484 (1983).

A.F. Bleikol, SPIE vol. 3314, p. 223, Jan. 1998.

Laser Focus World, Nov. 1998 p. S24.

*Primary Examiner*—Pedro Philogene
(74) *Attorney, Agent, or Firm*—Hahn, Loesser & Parks LLP; Alexander D. Bommarito

(57) ABSTRACT

A probe position sensing system for accurately determining a spatial location in a coordinate system of a distal end of a probe assembly. The probe assembly includes an articulated arm having a pair of sections interconnected by a flexible joint and at least one element. The element extends through the joint and is positioned to be subjected to a degree of flexure due to relative displacement of the sections. A flexure of the element induces a change in a physical property associated with the element. An instrument monitors the physical property and derives an angle between adjacent sections from variations of the physical property.

38 Claims, 12 Drawing Sheets

U.S. PATENT DOCUMENTS

| | | | |
|---|---|---|---|
| 5,307,437 A | 4/1994 | Facq et al. | 385/124 |
| 5,321,257 A | 6/1994 | Danisch | 250/227.16 |
| 5,558,091 A | 9/1996 | Acker et al. | |
| 5,563,967 A * | 10/1996 | Haake | 385/12 |
| 5,568,809 A | 10/1996 | Ben-Haim | |
| 5,600,300 A | 2/1997 | Povilaitis | |
| 5,600,330 A | 2/1997 | Blood | |
| 5,609,565 A * | 3/1997 | Nakamura | 600/229 |
| 5,633,494 A | 5/1997 | Danisch | 250/227.16 |
| 5,641,956 A | 6/1997 | Vengsarkar et al. | |
| 5,697,377 A | 12/1997 | Wittkampf | |
| 5,718,226 A | 2/1998 | Riza | |
| 5,770,155 A | 6/1998 | Dunphy et al. | |
| 5,817,005 A * | 10/1998 | Cohen | 600/201 |
| 5,899,425 A * | 5/1999 | Corey, Jr. et al. | 600/229 |
| 5,899,860 A | 5/1999 | Pfeiffer et al. | |
| 5,939,136 A | 8/1999 | Cronk et al. | |
| 5,983,126 A | 11/1999 | Wittkampf | |
| 6,016,371 A | 1/2000 | Wickham et al. | |
| 6,039,701 A | 3/2000 | Sliwa et al. | |
| 6,076,007 A | 6/2000 | England et al. | |
| 6,100,969 A | 8/2000 | Perez | |
| 6,113,588 A | 9/2000 | Duhaylongsod et al. | |
| 6,134,003 A | 10/2000 | Tearney et al. | |
| 6,155,984 A | 12/2000 | Krivitski | |

* cited by examiner

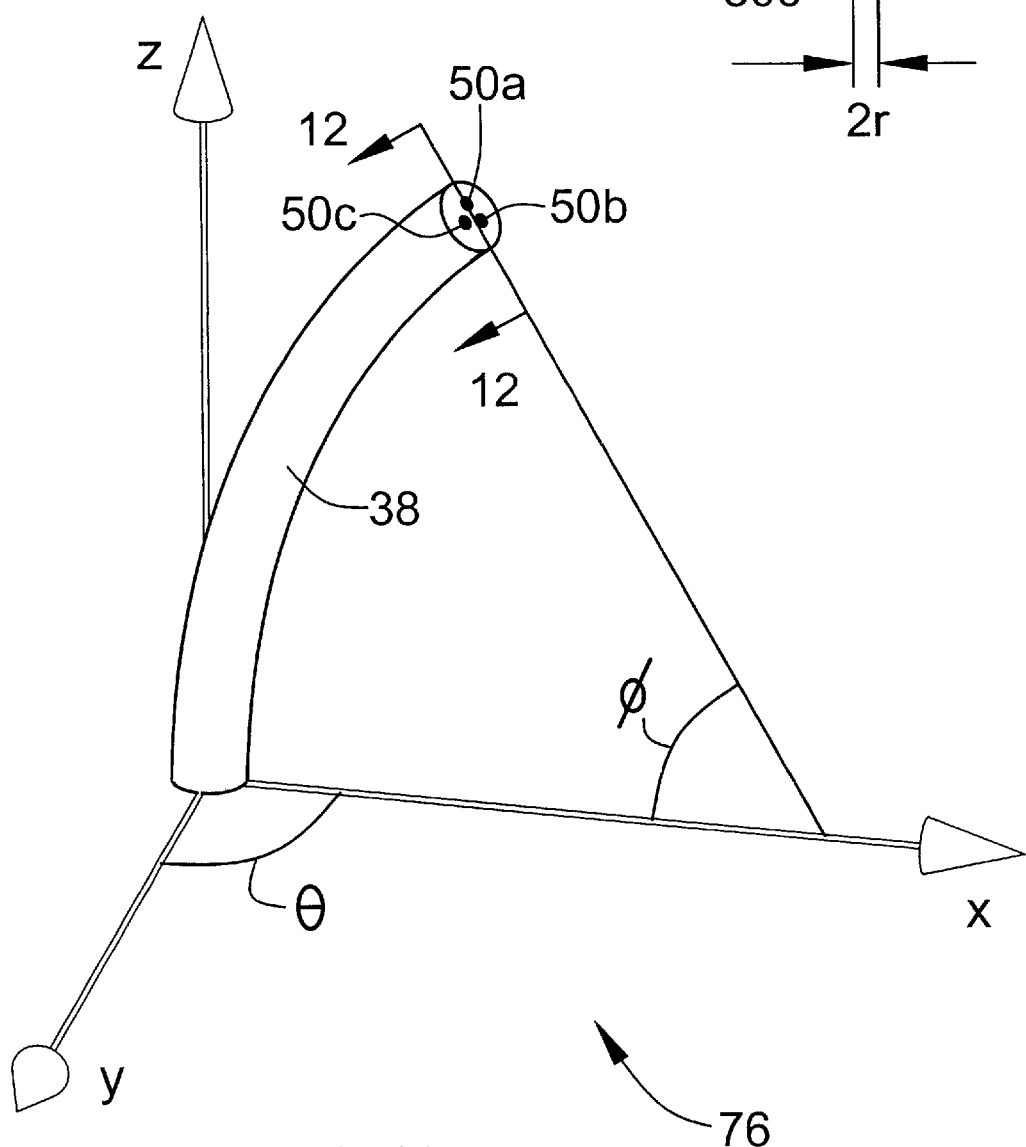
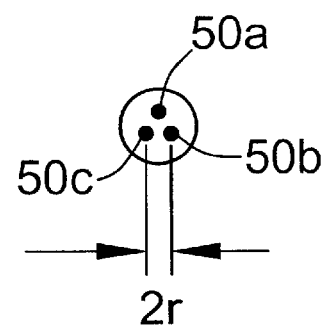
FIG. 11
FIG. 12

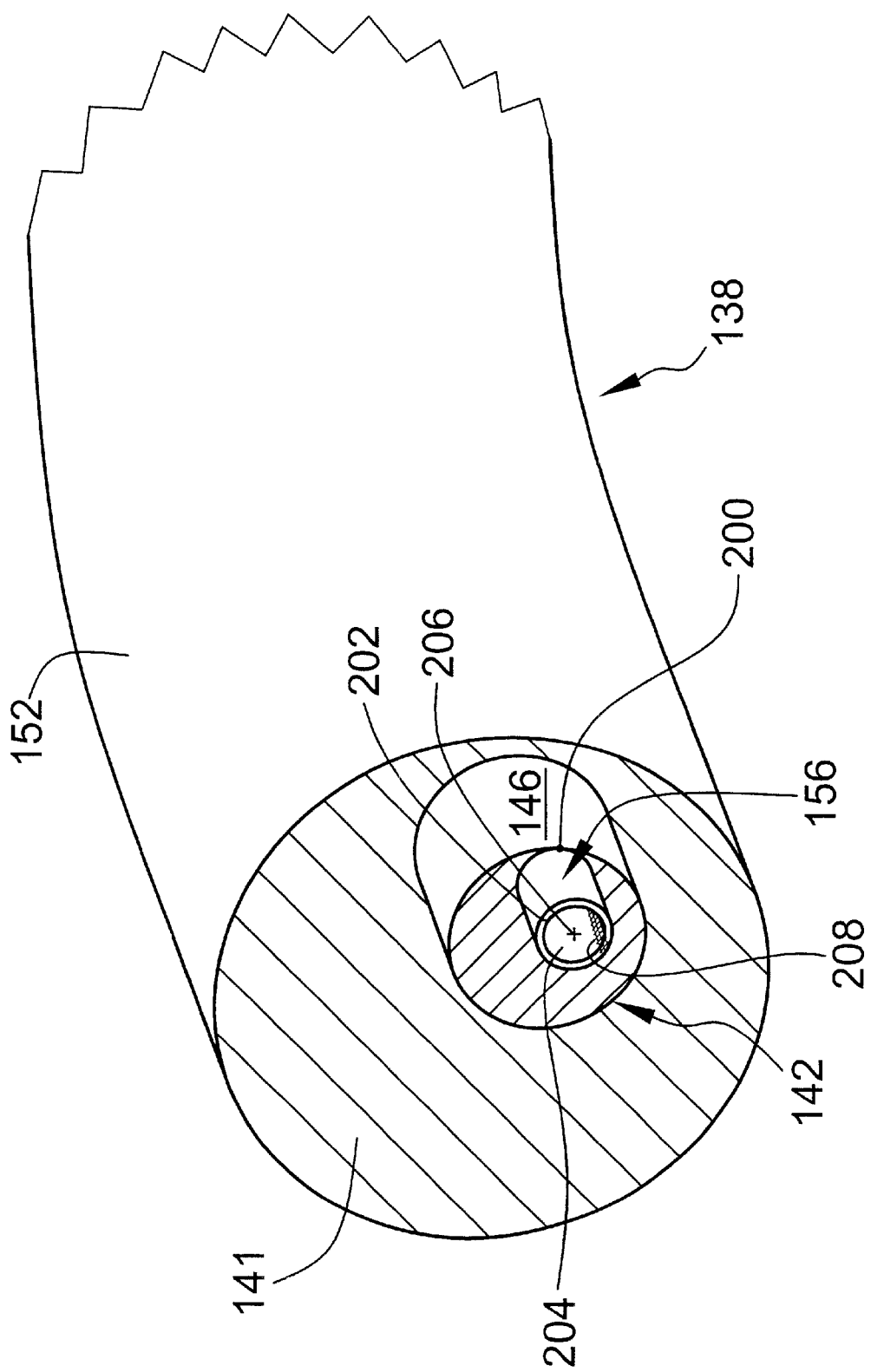

PROBE POSITION SENSING SYSTEM AND METHOD OF EMPLOYMENT OF SAME

RELATED APPLICATIONS

This application is a Continuation In Part Application of application Ser. No. 09/373,539 Filed on Aug. 13, 1999.

The present invention relates to a method and apparatus for determining the location in space of an end point of a multi-section, articulated arm assembly.

BACKGROUND OF THE INVENTION

Many procedures require an accurate location of a point in a coordinate system. For example critical medical procedures such as endoscopy, image guided surgery, or catheterization require a device and method for precisely locating a tip of a surgical instrument in three-dimensional space, either on the outer surface of a patients body or within the patient's body. Various techniques have been developed to perform this function in the prior art, based on the detection of changes in the strength and phase of electromagnetic fields, using a collection of optical sources and detectors arranged in a line of sight system, or using a mechanical arm with multiple straight sections and rotary encoders located at the mechanical joints between adjacent pairs of arms.

The electro-magnetic approach, examples of which are U.S. Pat. Nos. 5,568,809 and 5,600,300, measures a change in an electro-magnetic field due to changes in relative position and orientation between a transmitter and a receiver. This approach suffers from inaccuracies due to the inevitable presence of metals in the vicinity. For example, in an operating room environment, surgical instruments, illumination fixtures, tables, headrests, and immobilization and support structures all potentially interfere with the electro-magnetic approach. As a result, it is difficult for an electro-magnetic based positioning system to work reliably and accurately in a wide variety of settings in the presence of metals.

The line of sight approach determines the position and orientation of the tip of the assembly by pulsing the optical sources in a predetermined fashion and measuring the arrival times of the pulses at a multiplicity of optical detectors attached to the tip. This approach may be awkward to use in certain situations since it requires a user of the system and any attending personnel to take adequate care not to obstruct the detectors from the multiple optical sources. Proper location of the sources will avoid this in most instances.

In the mechanical approach, a series of coordinate angles between pairs of straight sections are measured by placing rotary encoders at the appropriate joints. The angle data is then used to calculate the tip position. The sheer size and limited range of motion typical of mechanical arm devices makes this approach cumbersome to use in a some environments.

It is therefore an object of the present invention to provide a probe measuring system in which the above disadvantages are obviated or mitigated.

SUMMARY OF THE INVENTION

In one aspect of the invention there is provided a probe position sensing system for determining a spatial location in a coordinate system of a portion of a probe assembly. The probe assembly includes an articulated arm having a pair of sections interconnected by a flexible joint and at least one element extending through the joint and positioned to be subjected to a degree of flexure due to relative displacement of the sections. A flexure of the element induces a change in a physical property associated with the element. The system includes an instrument to monitor the physical property and to derive an angle between adjacent sections from variations of the physical property.

In a further aspect of the invention, the probe position sensing system includes a stationary unit. The probe assembly connected to the unit and the probe assembly includes at least one articulated arm having a pair of sections interconnected by a flexible joint. At least one element extends through the joint and is positioned to be subjected to a degree of flexure due to relative displacement of the sections. A flexure of the element induces a change in a physical property associated with the element. At least one instrument is included in the system to monitor the physical property and to derive an angle between adjacent sections from variations of the physical property.

An additional aspect of the invention provides a method of determining a spatial location in a coordinate system of a portion of a probe assembly in a probe position measuring system. The system has a plurality of sections interconnected by corresponding flexible joints of known geometrical parameters. The method includes the steps of; identifying a predetermined fiducial location in the coordinate system; positioning the portion of the probe assembly at a desired location; measuring a variation of at least one property in a plurality of elements extending through the joint to determine the angular displacement of the arm from the predetermined fiduciary position; transmitting of the angle information to a computer; determining the spatial location of the portion of the probe assembly by combining the angle information and the geometrical parameters.

In a further aspect of the invention there is provided an articulated arm including a pair of sections and a flexible joint extending between and connecting the pair of sections. An element is located in the flexible joint and positioned to be subjected to a degree of flexure due to relative displacement of the sections. The element has a first longitudinal neutral axis and a sensor element having a second longitudinal axis contained in the element. The second longitudinal axis is in a spaced apart radial relationship with respect to the first longitudinal axis, wherein flexure of the sensor element induces a variation in a physical property associated with the sensor element, the variation used to derive an angle between adjacent sections.

The method may also include the steps of displaying the spatial location of the portion of the probe assembly on a display, superimposing an image on the display with the spatial location of the probe assembly, and following the movement of the image and computing the relative difference between the spatial location and the image.

BRIEF DESCRIPTION OF THE DRAWINGS

These and other features of the preferred embodiments of the invention will become more apparent in the following detailed description in which reference is made to the appended drawings wherein:

FIG. 11 is a representation of a flexible joint showing bend angle determination for a lumen with 3 fibers.

FIG. 12 is a section 12—12 of FIG. 11.

FIG. 14 is a further embodiment of FIG. 2.

DESCRIPTION OF THE PREFERRED EMBODIMENTS

Figure 1:
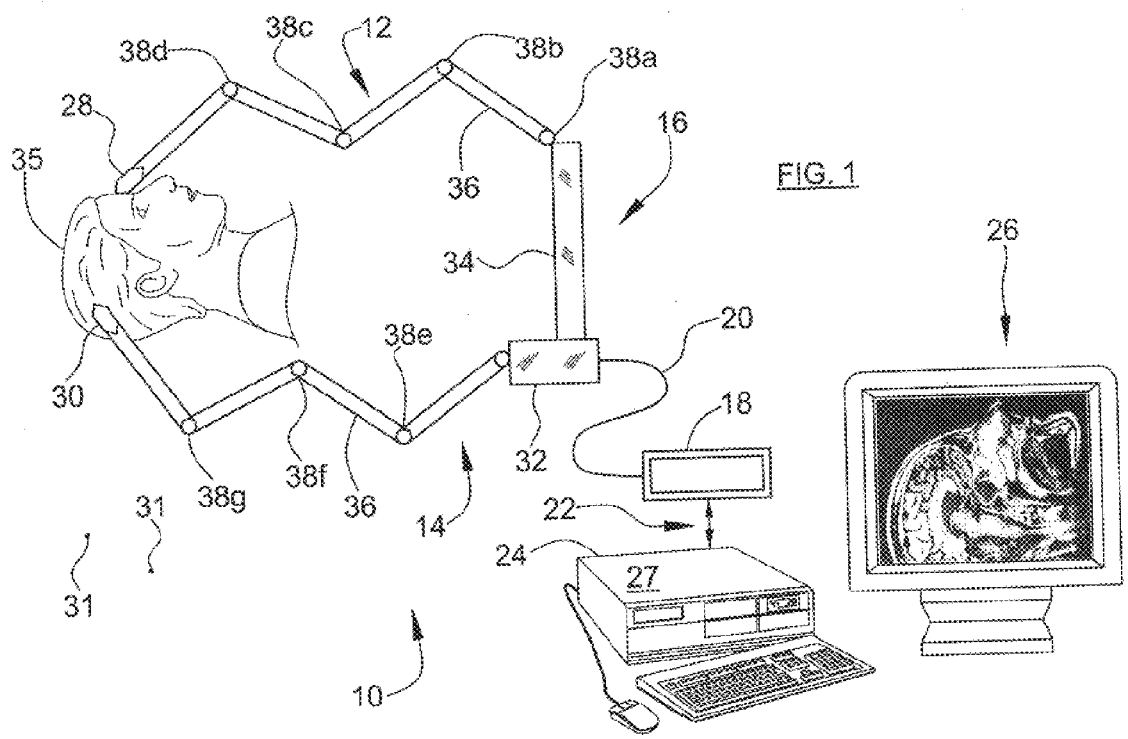
FIG. 1 is a schematic representation of a probe measuring system.

Referring to FIG. 1, a position sensing system 10 includes a probe assembly 12 to position a probe tip 28 adjacent to a patient 35 and a follower assembly 14 having a tip 30. The system 10 also includes a stationary unit 16 to provide support for assemblies 12, 14. The stationary unit consists of a base 32, usually positioned adjacent to the patient 35. Projecting upwards from the base 32 is a pedestal 34. The probe assembly 12 is connected to the pedestal 34 and the follower assembly 14 is connected to the base 32.

A signal processor 18 is connected to the unit 16 by a cable 20, including electrical and optical signals. The signal processor 18 includes sources for both optical and electrical signals and communicates with a computer 24 over a data link 22. Software 27 and a user interface 26 are associated with the computer 24 to indicate the quantified spatial positions of the probe tips 28, 30 within a coordinate system. The interface 26 may be interactive with a user (not shown) of the system 10, if desired. Other information known in the art, such as images, also may be displayed on the interface 26 if desired. In a medical application shown in FIG. 1, the relative position of the probe tip 28 to the follower tip 30 is displayed on a monitor and interfaced with a graphical representation of the patient 35. The follower assembly 14 is used to follow movement of the patient 35 if he cannot be immobilized so that the relative positions between patient 35 and the probe tip 28 can be determined. Therefore by following movement of the patient 35 and determining the relative positions between the tips 28 and 30, the display may be adjusted so that the accurate relative position of the tip 28 is indicated on the display.

Figure 2:
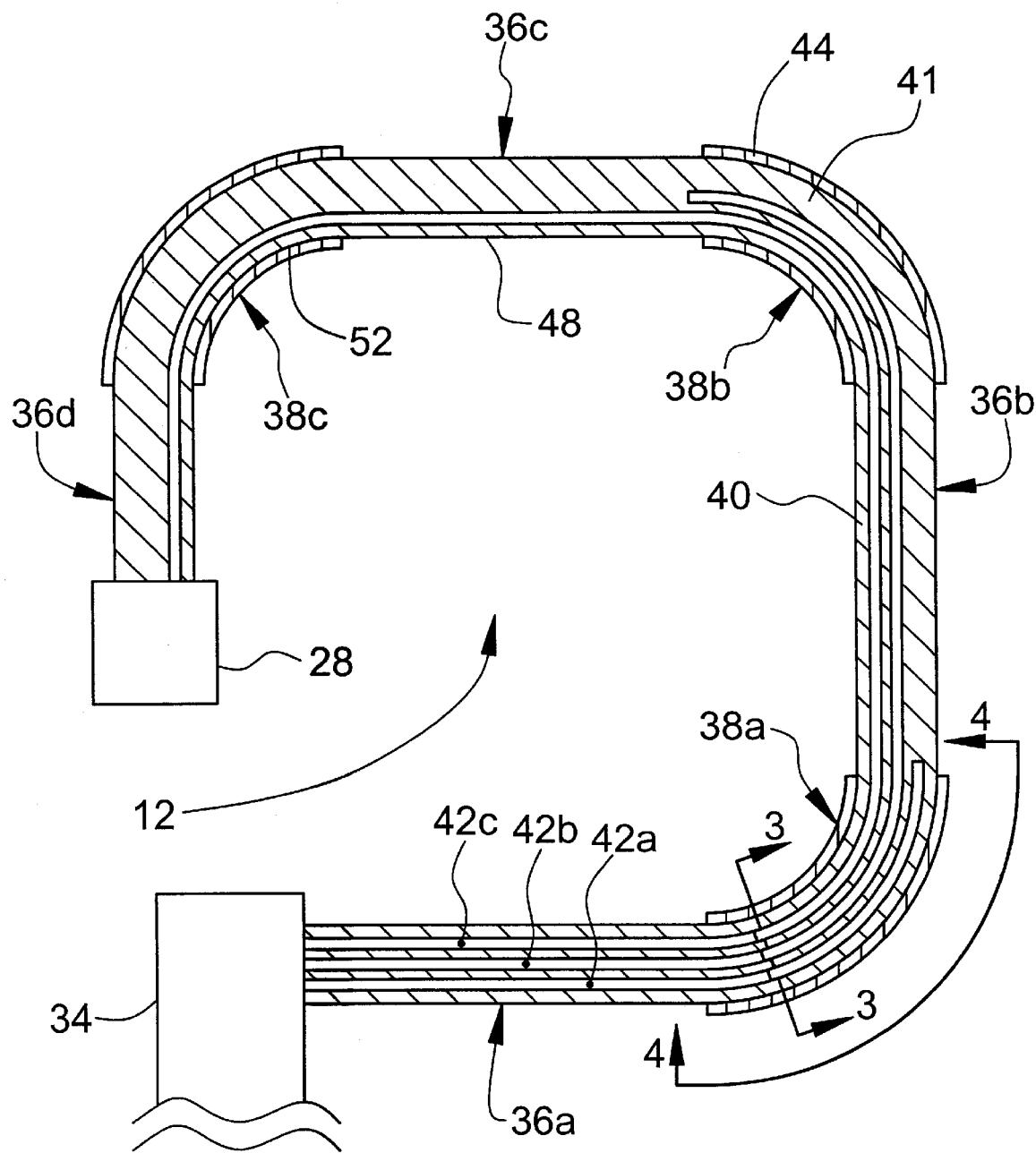
FIG. 2 is a section view of an arm shown in FIG. 1.

The probe assembly 12 is shown in more detail in FIGS. 1 and 2 as a plurality of rigid straight sections 36 interconnected to one another and to the pedestal 34 by respective flexible joints 38. A plurality of lumens 42 are housed in an interior 40, 41 of the sections 36 and joints 38 respectively and contain fiber optic cables 50 (FIG. 3) uniformly spaced from one another and from a central axis.

The probe assembly 12 may be used to identify particular locations or to support surgical tools for use by the surgeon. Since the follower assembly 14 is of a similar construction to that of the probe assembly 12, only the probe assembly 12 will be described in detail.

Referring to FIG. 2, a preferred embodiment of the probe assembly 12 includes joints 38 individually identified as 38a, 38b, 38c and 38d. Each joint 38 has an exterior wall 52 defining an interior 41. The interior 41 is filled with a flexible material compositionally compatible with the material of the wall 52. A number of straight sections 36 interconnect the joints 38 each having an exterior wall 48 defining an interior 40.

Figure 3:
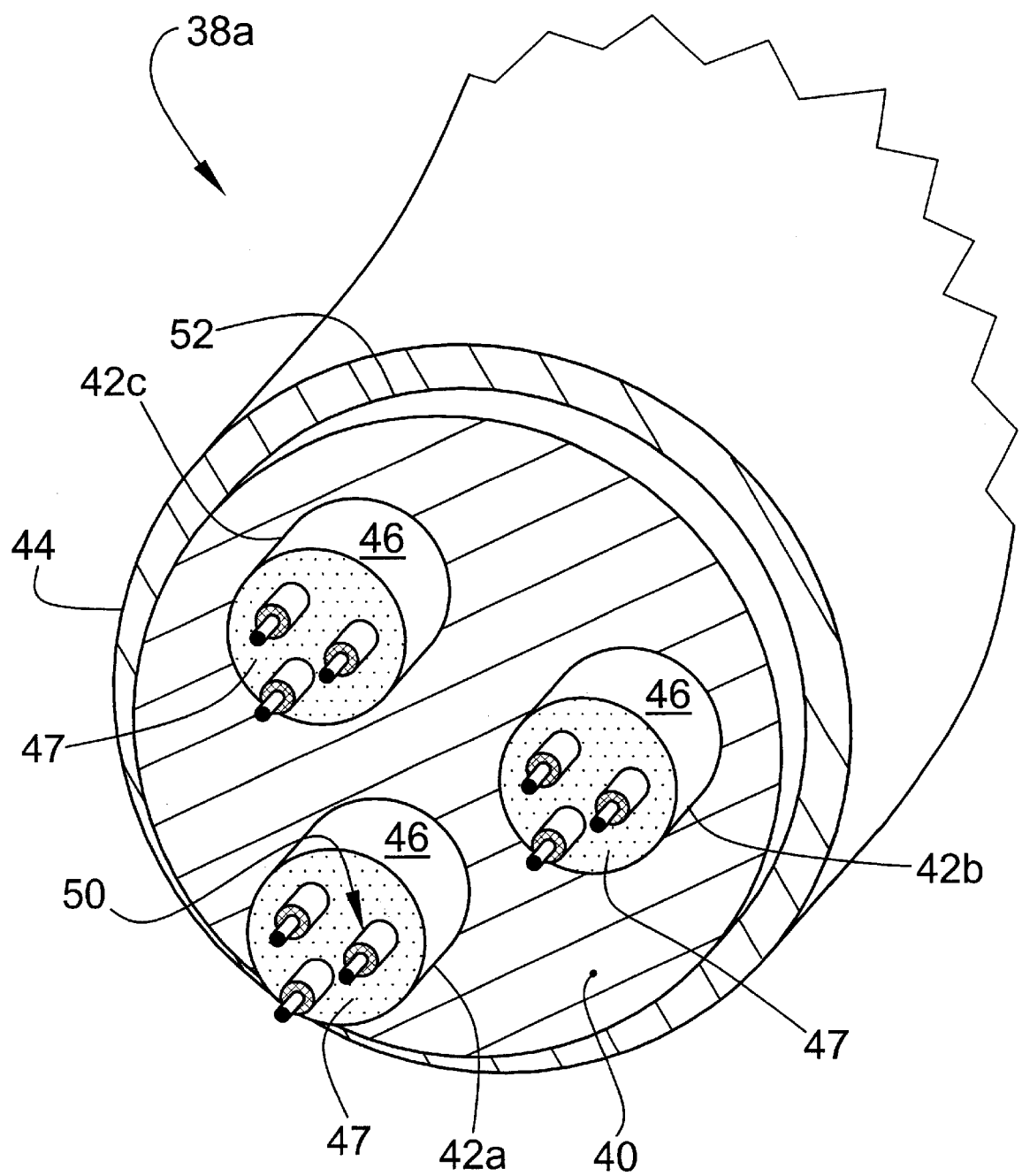
FIG. 3 is a perspective view of a section of line 3—3 of FIG. 2.

As can be seen in FIGS. 2 and 3, a series of three lumens 42a,b,c, or conduits, are positioned in the interiors 40, 41 of the sections 36 and joints 38. The lumens 42 act as passageways for sets of fiber optic cables 50 housed in the interiors 40,41. A respective one of the lumens 42 terminates at each joint 38, e.g. lumens 42a terminates at joint 38a and lumen 42b terminates at joint 38b etc.

Figure 4:
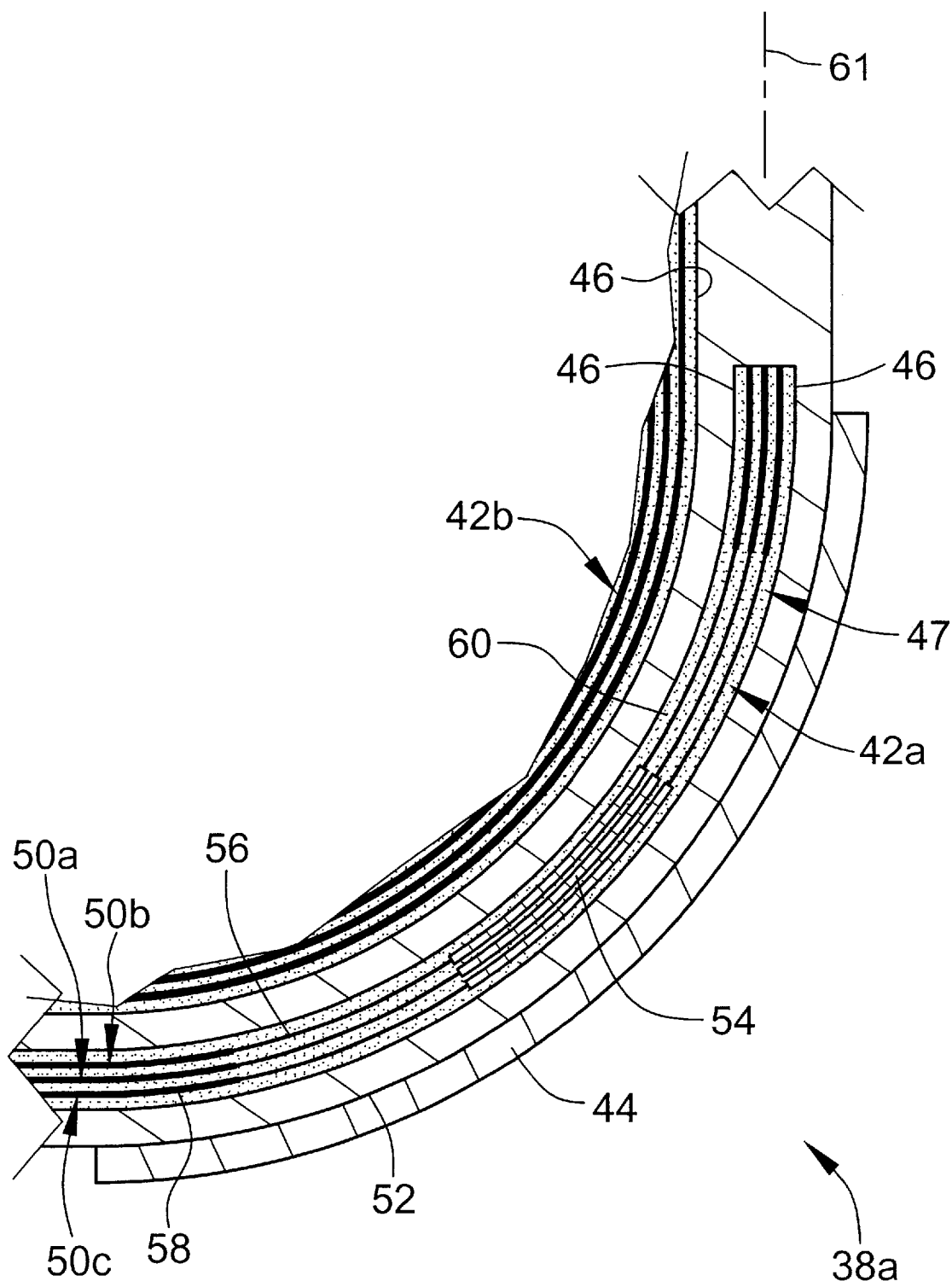
FIG. 4 is an enlarged cross-sectional view 4—4 of FIG. 2.

In FIG. 4, details of the interior 47 of a lumen 42 is shown for clarity. Each of the cables 50 includes a glass strand 56 having a protective coating 58. Each of the strands 56 of the cables 50, must be securely attached to the interior of the wall 46 in a manner which yields a strong, somewhat flexible bond. Possibility for slippage or hysteresis between the strands 56 and wall 46 must be controlled in order to transfer the desired strain magnitude directly from the joint 38a to the strands 56, upon flexure. As is described in further detail below, a bonding agent 60 may be used for adherence, which is compatible with the wall 46 of the lumen 42, the strands 56, and may be compatible with the coating 58 of the cables 50, 51 if desired.

Each of the strands 56 of the cables 50 in the lumen 42 that terminates at the particular joint 38, i.e. lumen 42a for joints 38a, includes a fiber optic Bragg Grating 54. The Grating 54 is positioned where it is subject to flexure of the strand 56 as the joint 38 is flexed. The Bragg Gratings 54 indicate a change in strain of the strand 56 by a change in reflected wavelength and so provide a signal indicative of the angular displacement of the sections 36 interconnected by the joint 38. The cables 50 in lumens 42 associated with other of the joints 38 do not include Bragg Gratings 54 and simply pass through the joints 38.

Figure 10:
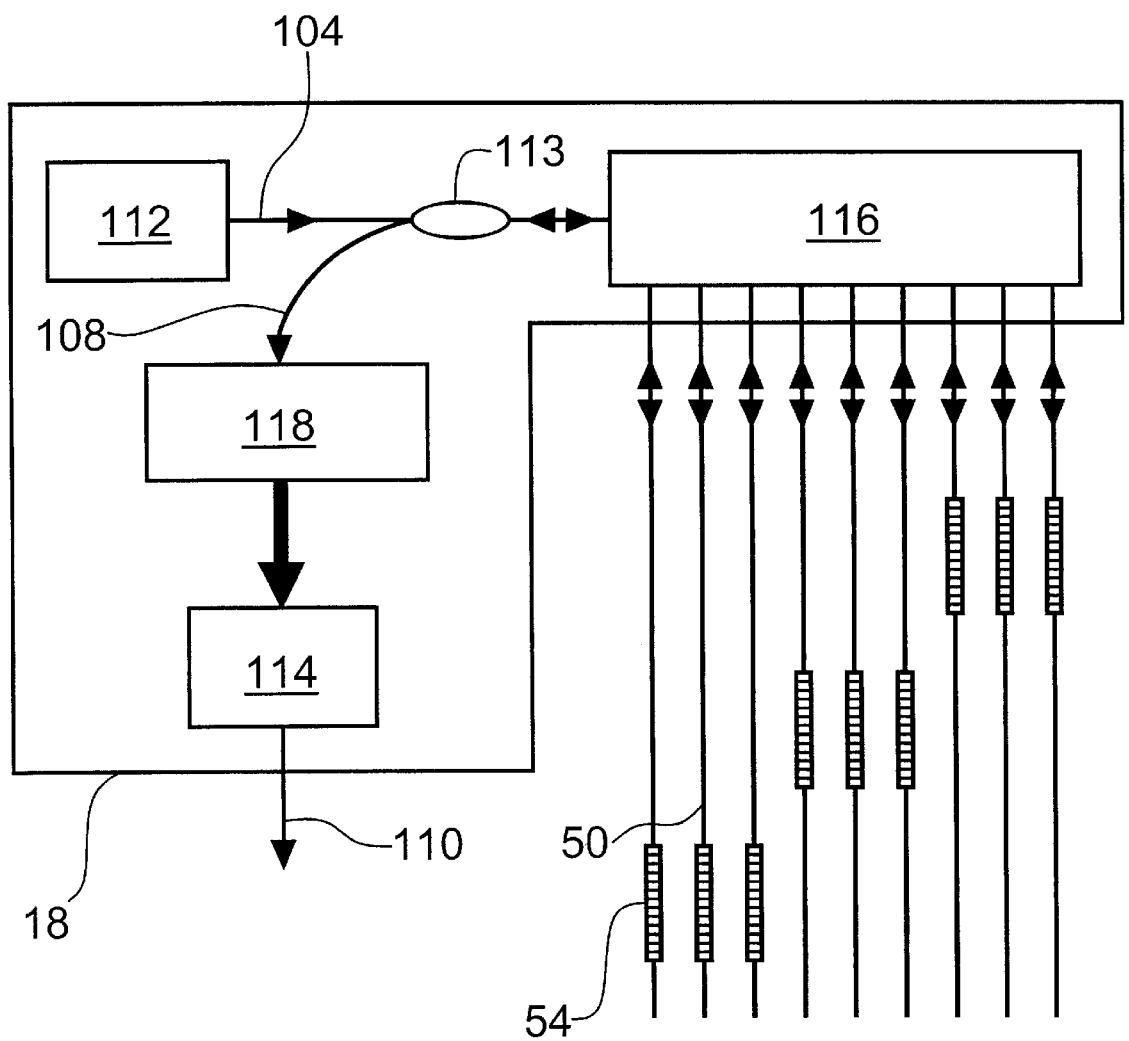
FIG. 10 shows components of a signal processor used in the system of FIG. 1.

The cables 50 extend from their respective joint of the probe assembly 12 back to the signal processor 18, which is shown in greater detail in FIG. 10. The signal processor 18 includes a multiplexer 116, which sequences the transmission of excitation optical signals 104 from a number of optical sources 112 to the cables 50. The multiplexer 116 also coordinates the receiving of reflected optical signals 108 from the FBGs 54 to a property filter 118. The property filter 118 measures a selected property of the reflected optical signals 108, such as wavelength in the case of FBGs 54. The selected property must vary as a function of the bend angles experienced by the joints 38 during flexure of the probe assembly 12. The property filter 118 transforms variations in the measured property of the original excitation optical signals 104 to variations in optical intensity. A series of photo detectors 114 transform the variations in optical intensity into electrical signals 110. The electric signals 110 are subsequently transmitted to the computer 24 as shown in FIG. 1. Changes in the strength of the electrical signals 110 are directly related to the degree of strain induced in the strands 56 of the cables 50. Differences in strain in each of the strands 56 of a set of cables 50 associated with a particular joint 38 are used to compute angular displacement of adjacent sections 36, relative to one another, to ultimately determine the position of the probe tip 28.

Operation of the probe positioning system 10 is now described with reference the medical application of FIG. 1. Each angle contained by each pair of adjacent sections 36 is measured in the strands 56 of each joint 38. The variations in the wavelength of the optical signals reflected by the FBGs 54 are transmitted through the stationary unit 16 to the signal processor 18. The signal processor 18 in turn transforms the reflected optical signals 108 into electrical signals 110, which are subsequently transmitted to the computer 24. Given the known lengths of the sections 36 and the relative disposition between the sections 36, the software 27 of the computer 24 quantifies the spatial position of the probe tip 28 in the coordinate system.

To establish the coordinate system, the probe tip 28 is positioned, either automatically or manually, at a number of predetermined locations to establish a datum. By locating the tip 28 at known locations as indicated at 31, the coordinate system may be established for the probe assembly 12. Typically the points 31 will be located on the stationary unit 16. After the probe assembly 12 is registered in the coordinate system, the patient is registered to the image by locating the tip 28 at distinctive positions on the patient that can be identified on the image. Movement of the tip 28 can then be followed on the image. Similarly, when the follower assembly 14 is used to follow movements of the patient, the difference in the positions of the tips 28, 30 is used to vary the position of the tip 28 on the image.

Figure 5:
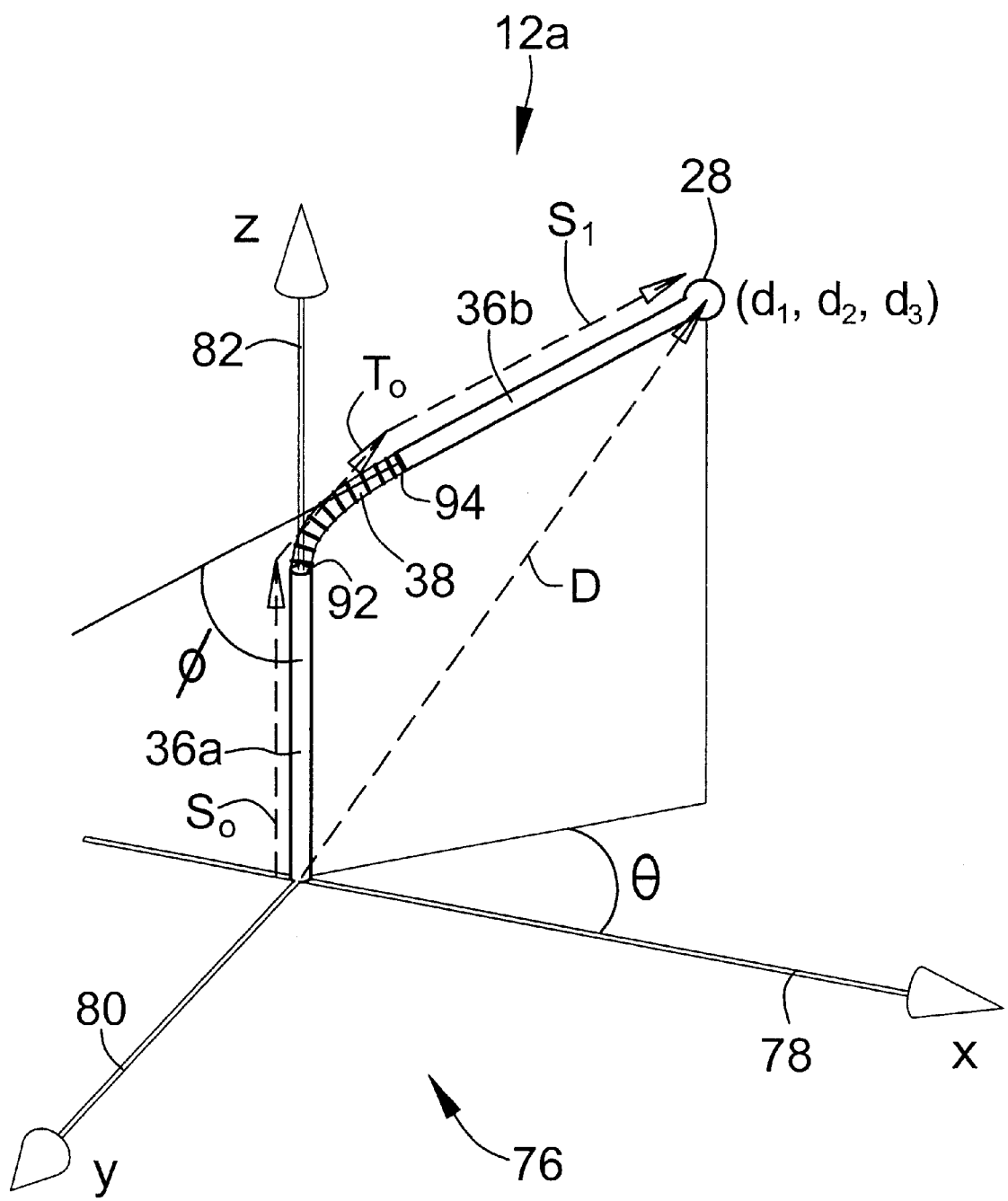
FIG. 5 is a diagrammatic representation of the arm of FIG. 2 in a coordinate system.

The computation of the location of the tip 28 is shown schematically with reference to FIG. 5 for exemplary purposes only. A probe assembly 12a has two sections 36a,b, and one flexible joint 38 there between. The probe assembly 12a is positioned in a three-dimensional coordinate system 76 defined by the axes 78, 80, and 82, traditionally referred to as the x, y, and z axes. The section 36a is situated along the z axis. The section 36b is inclined at the angle $\phi$ with respect to the axis 82 and rotated by the angle $\theta$ about the axis 82 measured with respect to the axis 78, in a plane defined by the axes 78 and 80.

The vector D ($d_1$, $d_2$, $d_3$) shown in ghosted view represents the spatial position of the probe tip 28 in the coordinate system 76, which is the resultant of three vectors $$D = S0 + T0 + S1, \quad (1)$$

where $S_0$ represents a vector describing the length and spatial orientation of the section 36a, $S_1$ represents a vector of the section 36b, and To represents a vector describing the length and spatial orientation from a distal end 92 of the section 36a to proximal end 94 of the section 36b.

It will be seen from FIG. 5 and using trigonometry, that the components of vector D can be described in the defined coordinate system 76 as $$d_1 = L \sin\phi \cos\theta + (J/\phi)(1-\cos\phi)\cos\theta, \quad (2a)$$

$$d_2 = L \sin\phi \sin\theta + (J/\phi)(1-\cos\phi)\sin\theta, \quad (2b)$$

$$d_3 = L \cos\phi + [L + (J/\phi)\sin\phi], \quad (2c)$$

where L represents the length from end to end of each of the straight sections 36a and 36b, and J represents an axially unchanged length of the joint 38 during flexure thereof.

In the above-described geometrical approach, to quantify the spatial position of the probe tip 28, the angles $\theta$ and $\phi$ are required. In the preferred embodiment, the strain induced in each of the strands 56, of the fiber optic cables 50, is measured by the FBGs 54 embedded therein. The working principles of the FBGs 54 for the purpose of strain measurement are well known in the art, wherein the strain, defined as $e=\Delta J/J$, and changes in temperature $\Delta T$ shift a center wavelength $\lambda_0$ of the light reflected by the FBGs 54. For typical off-the-shelf FBGs 54, such as those available from ElectroPhotonics Corporation, 3M Corporation, or Thor Labs, a normalized change in the wavelength is given as $$\frac{\Delta\lambda_i}{\lambda_0} = (0.79)e + 10^{-5}\Delta T, \quad (3)$$

where $\Delta\lambda_i$, represents the change in the wavelength of the light reflected in one of the cables 50 and $\lambda_o$ is the reference, or unstrained, wavelength of light reflected by the FBG 54.

The compound angle between the two sections 36a, 36b is determined from the three FBGs 54 in combination with three optical cables 50a,b,c contained within the lumen 42 associated with the particular joint 38. As illustrated in FIGS. 11 and 12, the strands 56a, 56b, 56c of respective cables 50a, 50b, 50c have induced strains $e_a$, $e_b$, $e_c$ respectively due to rotation from a datum through $\theta$ in the x-y plane and $\phi$ in the x-z plane. For ease of notation, let $$e_a = A \quad (4a)$$

$$e_b = B \quad (4b)$$

$$e_c = C \quad (4c)$$

and let $$AB = A - B \quad (5a)$$

$$CA = C - A \quad (5b)$$

$$BC = B - C, \quad (5c)$$

where the cables 50a,b,c are properly chosen to have a relative angular position, such that if cable 50a is placed at 0°, cable 50b is placed at 120°, and cable 50c is placed at 270°.

The calculation of bend angles $\phi$ and $\theta$ begins by forming the three ratios $$R1 = CA/BC \quad (6a)$$

$$R2 = AB/BC \quad (6b)$$

$$R3 = AB/CA. \quad (6c)$$

A set of three equations, one for each cable 50a,b,c, for each of the two bend angles $\phi$ and $\theta$ are constructed using geometry and the above ratios to give:

$$\cot\theta = -(2\sqrt{3})[R1 + (1/2)], \quad (7a)$$

$$\cot\theta = (2/\sqrt{3})[R2 + (1/2)], \quad (7b)$$

$$\cot\theta = (1/\sqrt{3})[(1-R3)/(1+R3)]; \quad (7c)$$

and $$\phi = BC/2r \sin(\theta), \quad (8a)$$

$$\phi = CA/2r \sin(\theta - 2\pi/3), \quad (8b)$$

$$\phi = AB/2r \sin(\theta - 4\pi/3), \quad (8c)$$

in which 2r represents a centre to centre spacing distance between adjacent cables 50.

Again, for notational convenience, let $$CT1 = -(2/\sqrt{3})[R1 + (1/2)], \quad (9a)$$

$$CT2 = (2/\sqrt{3})[R2 + (1/2)], \quad (9b)$$

$$CT3 = (1/\sqrt{3})[(1-R3)/(1+R3)]. \quad (9c)$$

These three values should all be equal where $$CT1 = CT2 = CT3 = \cotan(\theta) \quad (10)$$

and therefore $$\tan(\theta)=(1/CT1)=(1/CT2)=(1/CT3). \quad (11)$$

Since CT1, CT2, CT3 are indirectly dependent on the ratio of the induced strains, it is possible to determine the angle by monitoring the change in wavelength of the reflected light.

The angle $\theta$ is calculated using either its tangent form or its cotangent form, whichever is more accurate. To avoid ambiguity in the determination a lookup table, an example of which (Table T) is given below, is based on the signs of the strain differences AB, BC, and CA to determine the quadrant for $\theta$ in the coordinate system 76.

TABLE T.

QL = lower angle bound, QU = upper angle bound,
"+"= greater than zero. "−" = less than zero.

| BC | CA | AB | QL(deg) | QU(deg) | QL(rad) | QU(rad) |
|----|----|----|---------|---------|---------|---------|
| +  | +  | +  | ERR     | ERR     | ERR     | ERR     |
| −  | −  | −  | ERR     | ERR     | ERR     | ERR     |
| +  | −  | +  | 0       | 60      | 0       | $\pi/3$ |
| +  | +  | −  | 120     | 180     | $2\pi/3$| $\pi$   |
| +  | −  | −  | 60      | 120     | $\pi/3$ | $2\pi/3$|
| −  | +  | +  | 240     | 300     | $4\pi/3$| $5\pi/3$|
| −  | −  | +  | 300     | 360     | $5\pi/3$| $2\pi$  |
| −  | +  | −  | 180     | 240     | $\pi$   | $4\pi/3$|

It should be noted that the triply redundant calculation of angle $\theta$ gives a method for detecting system errors which lead to nonidentical errors in the FBGs 54, and that the effects of system noise can be reduced by taking the average value given as:

$$\theta=(1/3)[\arctan(1/CT1)+\arctan(1/CT2)+\arctan(1/CT3)]. \quad (12)$$

Similarly to determine $\phi$, let PHI1, PHI2, and PHI3 denote the three values of $\phi$ calculated using the previously described three equations. Then $$PHI1=BC/[2r\sin(\theta)], \quad (13a)$$

$$PHI2=CA/[2r\sin(\theta-2\pi/3)], \quad (13b)$$

and $$PHI3=AB/[2r\sin(\theta-4\pi/3)]. \quad (13c)$$

In practice, assume $\phi$ is defined only over the range 0 to $\pi$. Then its values are obtained directly by these equations with no need for a lookup table. Again, taking advantage of the redundant calculation of $\phi$ the average value is $$\phi=(1/3)[PHI1+PHI2+PHI3]. \quad (14)$$

Once the angles $\phi$ and $\theta$ are known, the calculation for the position of the distal tip 28 of the probe assembly 12a is made using above stated equations for the vector D, namely equations 2a, 2b and 2c.

It will be appreciated that this measurement and computation is performed at each of the joints 38 with the cables 50 in the lumen 42 associated with that joint and the position of the tip 28 from the datum observed.

During the initialization of the system 10 described above, it may be necessary to determine "offset" strains present in the strands 56 of each of the joints 38. Offset strains can be a result of the manufacturing process for the probe assembly 12 or initial displacement thereof. The offsets can be determined by utilizing a number of points during initialization. Let $\{P1(x_1,y_1,z_1), P2(x_2,y_2,z_2), \ldots PN(x_N,y_N,z_N)\}$ be a collection of known points in the user-defined coordinate system. These points may be referred to as calibration points 31 as shown in FIG. 1. The number of calibration points 31 required depends on the physical characteristics of each particular probe assembly 12. Let $\{(\theta_{01},\phi_{01}),(\theta_{02},\phi_{02}),\ldots(\theta_{0N},\phi_{0N})\}$ be a set of angles initially measured between adjacent pairs of straight sections 36, where the distal end 28 of the assembly 12 is located at the reference points P1, P2, ... PN respectively. Let $\{((\theta_1,\phi_1),(\theta_2,\phi_2),\ldots(\theta_N,\phi_N)\}$ be the actual or desired bend angles. Given that the relative location of the calibration points is known, it is possible to identify the residual strains and compensate for them in further measurements. The number and location of the calibration points are chosen to uniquely determine offset strains, and gain factors for the system such that the signal processing yields numerically correct values of the bend angles in a user-defined coordinate system.

Figure 6:
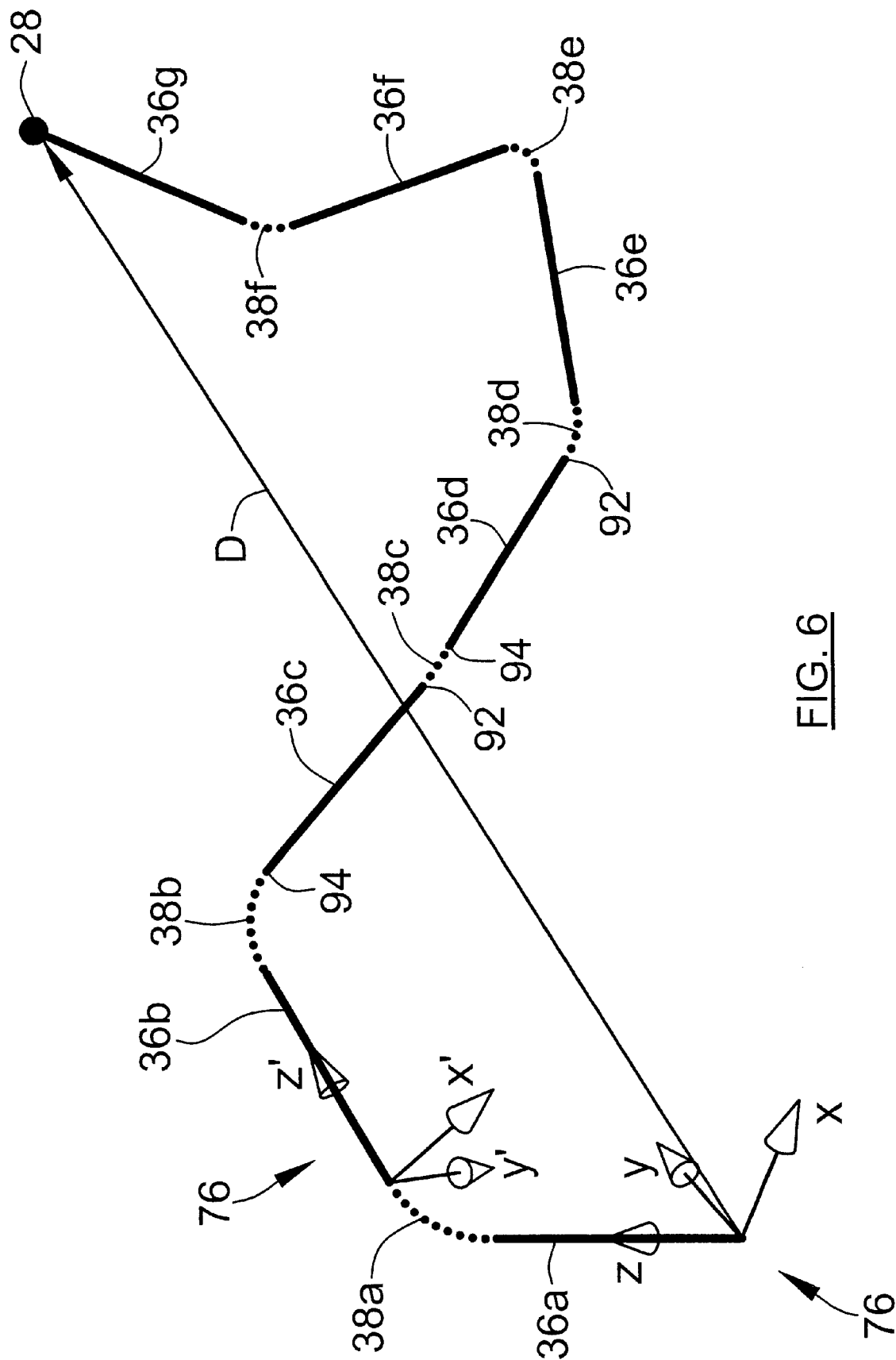
FIG. 6 is a diagram similar to FIG. 5 of a multiple segment arm.

Extensions of the above described calculation for vector D can be used to calculate a position of a probe tip 28 for an arrangement of multiple rigid sections 36 and flexible joints 38 as shown in FIG. 6. A proximal end 94 of each rigid section 36 is considered to be an origin (0,0,0) of a new "local" coordinate system in which the rigid section 36 points along the z axis with a distal end 92 located at (0,0,L) as shown in FIG. 6. The flexible joints 38 then effectively perform a rigid body coordinate transformation between the local coordinate systems defined by adjacent straight sections 36 so that the displacement of each section 36 from an origin is derived additively.

The particular properties required for the optical source 112 depends on the particular optical property chosen for measurement In the case of FBGs 54, the optical source 112 is typically chosen to have the following characteristics
(a) a center wavelength of approximately 1300 nm,
(b) an average spectral width greater than 20 nm, and
(c) an average output power greater than 100 nW.

The optical source 112 is also preferably contained in a package that is easily mated optically with the single mode fiber optic cables 50. The average optical power of the source 112 should be high enough so that there is sufficient signal strength present at the photo detector 114 after the excitation signals 104 have traveled to the FBG 54, and reflected by the FBG 54 in a narrow range of wavelength centered on the FBG 54 center wavelength, back through the cables 50 to the photo detector 114. In some situations, it may be necessary to use multiple optical sources 112 in order to maintain sufficient optical signal strength at the photo detector 114.

To extract the measurement of the angle, the signal processor 18 measures the change of a selected property of the optical signal 104, such as amplitude, frequency, wavelength, phase, or polarization state supplied by the optical source 112, as a function of the change in the bend angle of the flexible joint 38 (shown in FIG. 1). Hence, the signal processor 18 includes a property filter 118 for measuring specially that optical property which varies as a function of bend angle. The property filter 118 converts a change in the desired optical property into a change in optical intensity which is incident on photodetectors 114 to provide a varying electrical signal 110. The center wavelength of light reflected from the FBGs 54 depends on the length of the FBGs 54. The length of the FBG 54 changes in proportion to the induced strain, the magnitude of which is dependent on the magnitude of the bend angle due to flexure of the flexible joint 38. Various well-known means are available to determine the wavelength of light including interferometers such as Fabry-Perot cavities, Michelson interferometers, Mach-Zehnder interferometers, Sagnac interferometers, and dispersive elements including ruled gratings (both transmissive and reflective), and Echelle gratings.

The photo detector 114 is chosen to be compatible with the light received from the property filter 118 in order to provide an electrical signal 110 with sufficiently high signal to noise ratio. A wide selection of photo detectors 114 is currently available from a variety of vendors, such as Newport Corporation, New Focus, and Hewlett-Packard.

Typically it is neither necessary nor cost effective to use one optical source 112 and one photo detector 114 for each fiber optic cable 50 in the system 10. A multiplexer 116 can be used to distribute light from the source 112 sequentially to the lumens 42 associated with the respective joints 38 and sequentially among the cables 50 in each lumen 42. The multiplexer 116 also receives light from the cables 50 and directs it to the property filter 118 again in a known, controlled manner. For example, in the case of FBGs 54 embedded in multiple cables 50 an electrically-controlled optical switch 113 may be used to deliver light from the optical source 112 in succession to each of the multiple cables 50. While the source 112 is "connected" to a particular set of cables 50 in a particular joint 38, the light returning from each cable is directed to the property filter 118 to complete the measurement of each of the FBGs 54 in that flexible joint.

Fabrication of the flexible joint 38 can be accomplished by embedding the FBGs 54 in the strands 56 of the respective cables 50, and the cables 50 in the lumen 42 of an appropriately chosen tubing material. A three cable configuration will be described for exemplary purposes only with reference to FIG. 4, although it will be appreciated that an extension to a four or more cable configuration is straightforward.

In the case where a coating 58 is used, the coating 58 is first stripped away from the strand 56 in the vicinity of the embedded FBGs 54. The three cables 50 are glued together to form a "bundle" using a suitable adhesive such as an ultraviolet (UV) curable adhesive NOA 68 from Norland Products Incorporated (New Brunswick, N.J.). After the adhesive has cured, the three cable bundle is inserted into a lumen 42 of the tubing, such as the multi-lumen silicone joint tubing manufactured by Vesta, Incorporated (Franklin, Wis.) or the multi-lumen polyimide tubing manufactured by Putman Plastics (Dayville, Conn.). A suitable adhesive is injected into the lumen 42 containing the cable bundle, in order to completely fill the void space between the outer surface of the cable bundle and the inner surface of the lumen 46. By curing the adhesive, the exposed strands 56 become mechanically embedded in the tubing and thus the strain in the tubing due to flexure of the joint 38 is transferred directly to the strands 56, where it is subsequently measured as a change in reflected wavelength of the FBGs 54.

Various techniques can be used to provide the requisite flexure strength, bend uniformity, and kink resistance in the flexible joint to inhibit axial compression or expansion of the flexible joint to a negligible magnitude. The requisite tube properties may be obtained by varying the tubing material, size, and type of structural reinforcement 44 of the wall 52. One reinforcement technique is to choose tubing with an embedded braid. Another technique is to wrap a plurality of wires on the outside of the tubing wall 52.

The tubing material may be any polymeric or nonpolymeric material suitable for the particular application. For medical applications, suitable materials include silicone, polyetheretherketone (PEEK), polyimide, and polyurethane. It is possible to obtain multi-lumen tubing in which the interior wall of the lumen 42 is of a different material than the tubing itself The sections 36 are preferably composed of rigid tubing, either axially straight or arcuate. In the case of arcuate shaped sections, suitable adjustment may be made in the above mentioned formulas.

The flexibility of the joints 38 is limited, in order to control the maximum magnitude of the strain to which the fiber optic cables 50 are subjected. Strain values in excess of a few percent can lead to premature failure and therefore should be avoided.

In general, upon bending the flexible joint 38, the strain in the strand 56 is less than the strain in the joint material. The ratio of these values, sometimes referred to as "strain transfer efficiency", depends on the strength of the bond between the strand 56 and the surrounding material 47, and on the mechanical properties of the surrounding material 47 itself. Hence, it is possible to design the flexible joint 38 such that, although the strain in the joint material is larger than a few percent, the strain in the strand 56 is safely less than a few percent. This safety arrangement can be at the expense of reduced angle accuracy at small bend angles. Conversely, the flexible joint materials may be chosen such that the strain transfer efficiency is nearly unity but then care should be taken to restrict the bend angles to values small enough to prevent mechanical failure of the strands 56. In addition, for a given bend angle and joint material and geometry, the strain experienced by the strands 56 depends on the location of the strands 56 relative to the neutral bend axis 61 of the joint 38, with strain increasing with increasing radial distance from the neutral axis 61.

Therefore, from an engineering standpoint, the amount of strand strain per unit change in the angle can be controlled by the choice of strand location relative to the neutral axis 61, bond strength between the strand 56 and the joint material, and joint material itself. As an example, for a flexible joint 38 comprising the aforementioned Norland NOA 68 epoxy and a teflon tube, with the fibers placed within 500 um of the neutral axis 61, strain transfer efficiency of approximately 68% was measured.

It is understood that it is possible to draw or extrude the cables 50 along with the tubing during fabrication, thereby eliminating the need for lumens 42 and a bonding agent 60. The choice of bonded or extruded cables 50 for a particular application may be based on manufacturing considerations. In addition, it is understood that the cables 50 may be embedded in the flexible joint during manufacture thereof without the need for extrusion.

Figure 9:
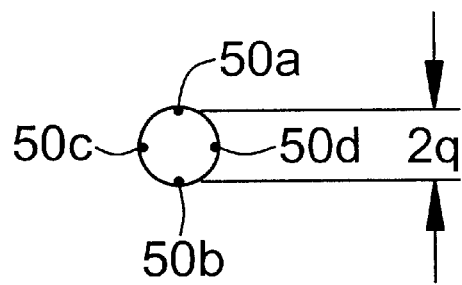
FIG. 9 is a section 9—9 of FIG. 8.
Figure 8:
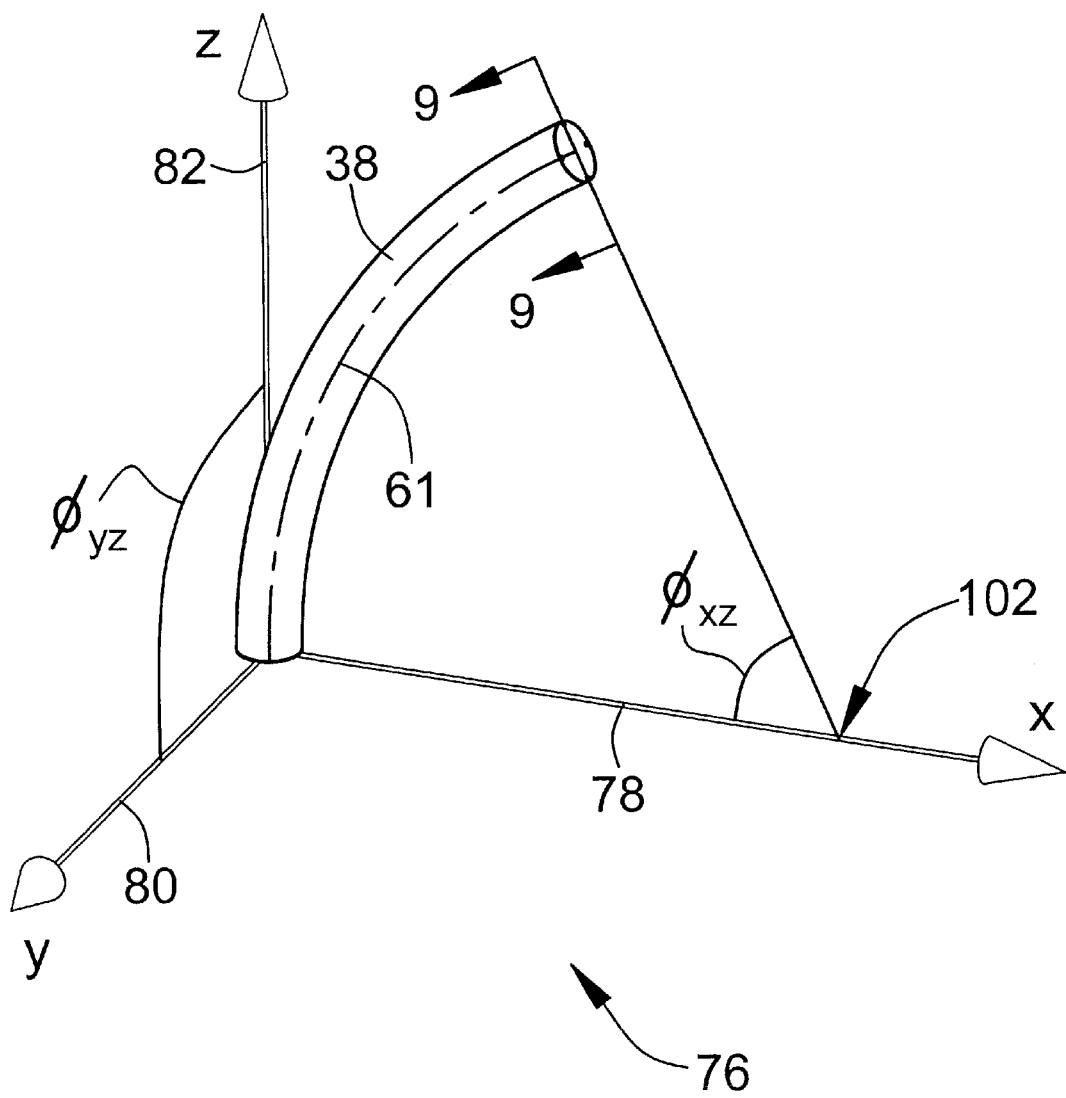
FIG. 8 is a view of an alternative lumen arrangement.

In the above embodiment, three cables 50 are used to obtain an angular measurement. As an alternative, as shown in FIGS. 8 and 9, a pair of angles $\phi_{xz}$ and $\phi_{yz}$ are determined through the wavelength changes of light in four fiber optic cables 50a,b,c,d due to flexure of the joint 38. Cables 50c, 50d are situated in a plane containing the neutral axis 61 and parallel to the axis of rotation, i.e. the y axis. The cables 50a,b are positioned by an amount q to either side of the axis 61 radially inward and outward with respect to the center of curvature 102. A flexure of the joint 38 in the x-z plane through the angle $\phi_{xz}$ results in the wavelength of reflected light of the cable 50d remaining constant, whereas the wavelength of the reflected light in cable 50b decreases by an amount $\Delta\lambda_{50b}$, and the wavelength of the cable 50a increases by $\Delta\lambda_{50a}$. In this case, the angle $\phi_{xz}$ is determined by $$\phi_{xz} = \frac{B}{2(0.79)q}\left(\frac{\Delta\lambda_{50a}}{\lambda_0} - \frac{\Delta\lambda_{50b}}{\lambda_0}\right), \quad (3)$$

assuming ΔT=0.

In the case where the bend is contained in the y-z plane, the cables 50c,d are used to give the angle $\phi_{yz}$ as $$\phi_{yz} = \frac{B}{2(0.79)q}\left(\frac{\Delta\lambda_{50d}}{\lambda_0} - \frac{\Delta\lambda_{50c}}{\lambda_0}\right). \quad (4)$$

Having computed $\phi_{xz}$ and $\phi_{yz}$ the angles corresponding to φ and θ in FIG. 5 can be determined uniquely for an arbitrary orientation of a bend plane not on the x-z or y-z planes by the relations $$\phi = \frac{\phi_{xz} + \phi_{yz}}{2} \quad (5)$$

and $$\tan\theta = \frac{\phi_{xz}}{\phi_{yz}}. \quad (6)$$

Figure 7:
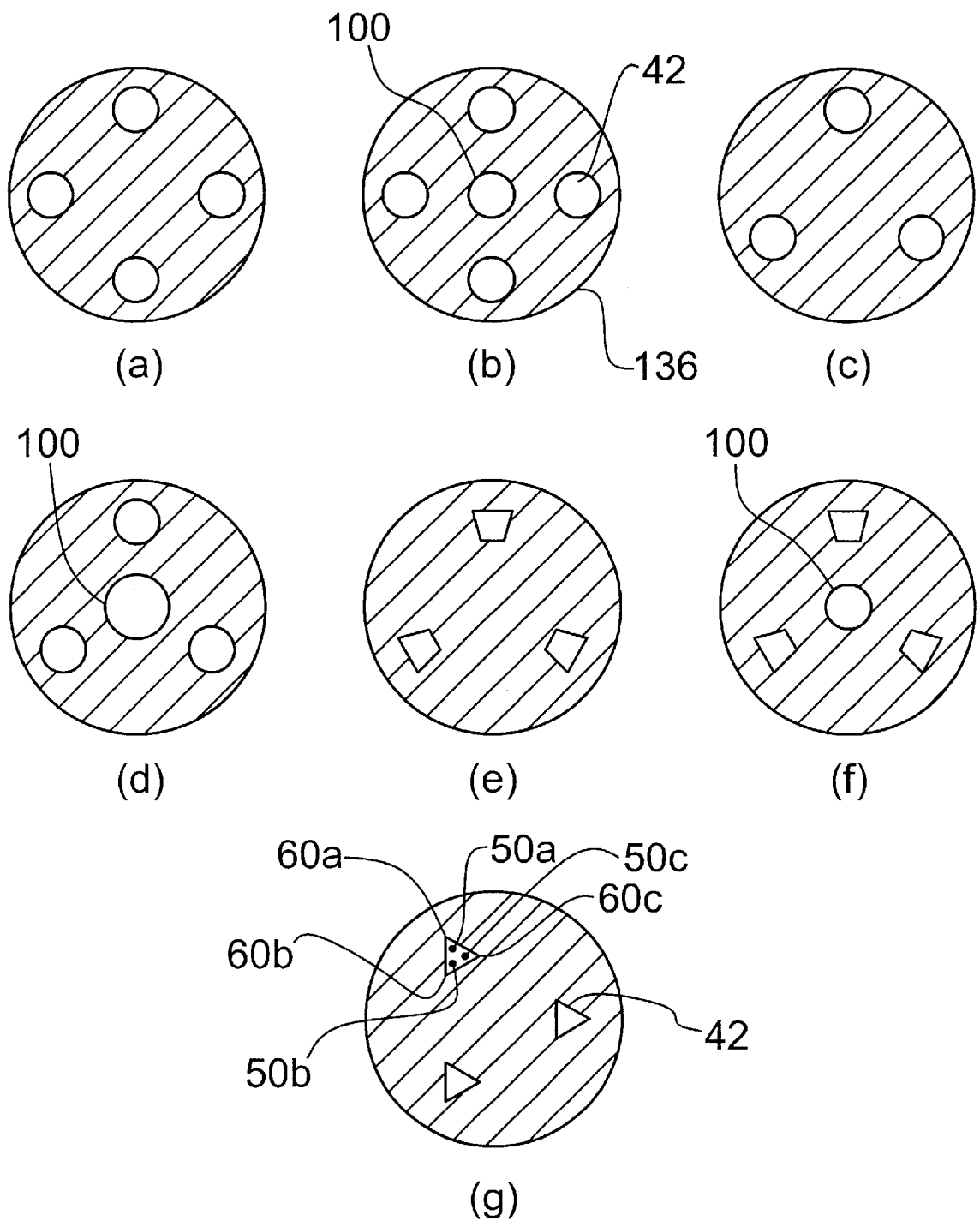
FIG. 7 are alternative arrangements of lumens in the arms of FIG. 2.

The lumens 42 may be arranged within the arms in a number of different ways as shown in FIG. 7. The configurations shown in 7a and 7b, four lumens 42 are shown for use with four joints 38 as in the arm of FIG. 1. Similarly, for a three joint arm, the arrangements of FIGS. 7c to 7f may be used. An additional lumen may be provided on the neutral axis 100 as shown in FIGS. 7b and 7d to accommodate additional sensors, wires, or fiber optic cables not required by the angle measurement system.

A particular cross sectional shape of the lumens 42, as shown in FIG. 7g, can be employed to facilitate proper positioning of the strands 56 on the wall 46 of the lumen 42 during fabrication of the joint 38. In this example, the three cable 50a,b,c configuration of FIG. 11 is facilitated at the relative angular positions of 0° of cable 50a, 120° of cable 50b and 270° of cable 50c, located at the vertices 60a, 60b, 60c respectively of the triangular cross sectional shape of the lumen 42.

It is recognized that other optical approaches can be used for bend angle determination, including changes in intensity of light propagating in a fiber due to bend angle and changes in spectral properties of light as a function of viewing angle. It is also appreciated that strands 56 may be positioned directly on the wall 52 of the joint 38 rather than on the wall 46 of the lumens 42.

Accordingly by monitoring the signal differences in the pairs of strands 56 in each lumen 42, the angle between the adjacent sections can be determined. The Bragg Gratings 54 measure strain, i.e. changes in length of the elements and indicate strain by a change in reflected wavelength. Similar principles may be used with non optical elements, such as strain gauges incorporated into wire filaments, so that indicated strain may be measured and the corresponding angles computed.

In general, the angle $\phi_{xz}$ is determined from the changes in the length of the filaments by $$\phi_{xz} = \frac{\Delta l_{50a} - \Delta l_{50b}}{2q},$$

where Δl represents a change in length of the filament 50a,b.

In the case where the bend is contained in the y-z plane, the fourth filament 50d is used to give the angle $\phi_{yz}$ as $$\phi_{yz} = \frac{\Delta l_{50d} - \Delta l_{50c}}{2q}.$$

As above, the bend angles φ and θ can be determined uniquely for an arbitrary orientation of a bend plane not on the x-z or y-z axes by the relations $$\phi = \frac{\phi_{xz} + \phi_{yz}}{2}$$

and $$\tan\theta = \frac{\phi_{xz}}{\phi_{yz}}.$$

It should be noted that any other strand arrangement including at least three strands can also be used and the appropriate equations can be derived using a modified version of the above described method.

Figure 13:
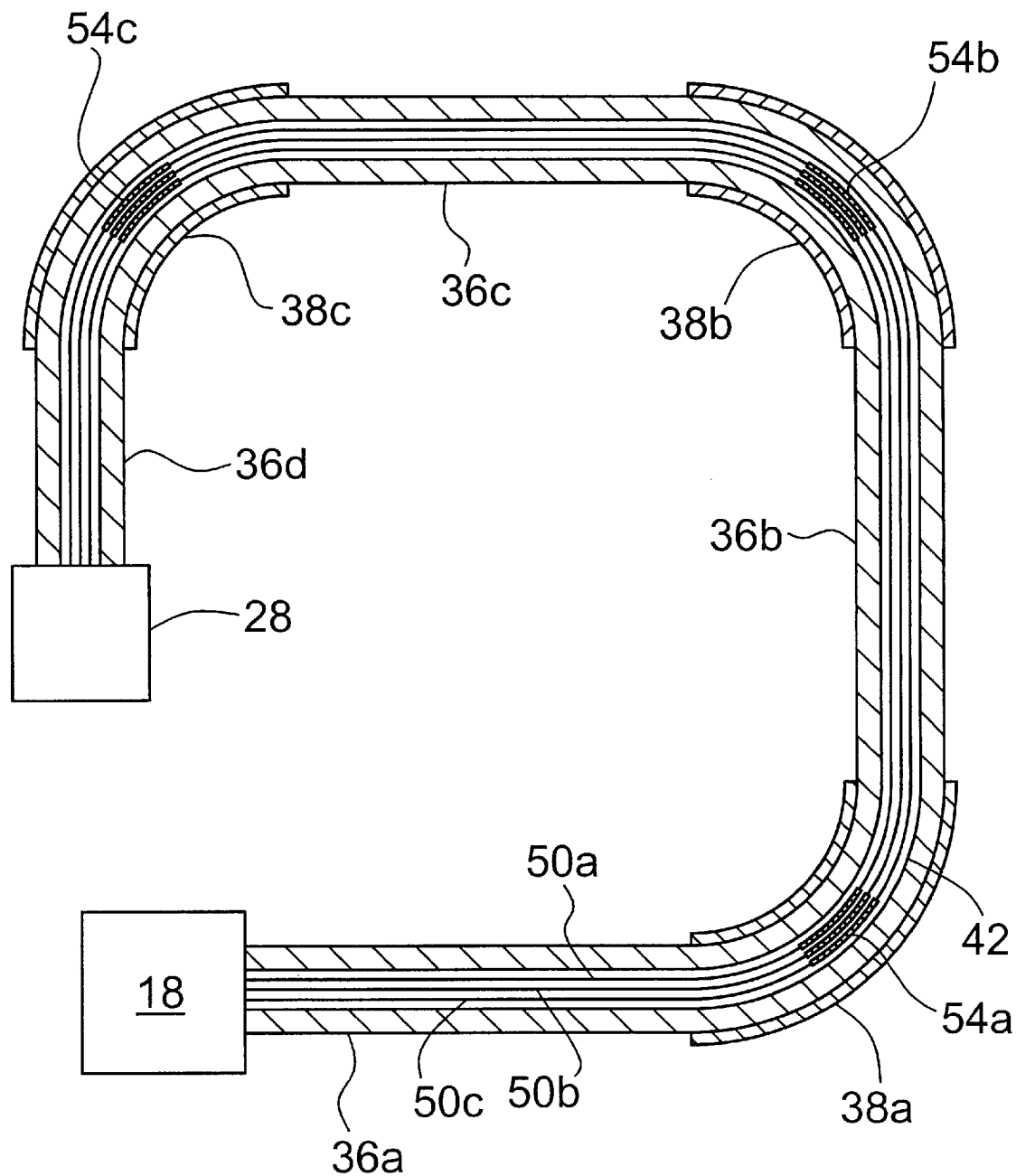
FIG. 13 is an alternative embodiment of FIG. 2.

A further embodiment shown in FIG. 13 utilizes the properties of Fiber Bragg Gratings 54 at each joint 38, but has a single lumen 42 extending between each of the joints 38 and the signal processor 18. Referring to FIG. 13, a common lumen 42 having fiber optic cables 50 extends through each of the flexible joints 38. For exemplary purposes only, the lumen 42 with three cables 50 is employed for all of the joints 38a,b,c. Each of the cables 50 extends from the signal processor 18 through to the most distal joint 38c. Separate sets of three FBGs 54a,b,c, i.e. 54a for joint 38a etc., are embedded in each of the strands 56 of the cables 50 associated with each of the joints 38a,b,c respectively Each set of FBGs 54 reflects variations in a separate and distinct center wavelength back to the signal processor 18. A suitable property filter 118, or filter array, is employed so as to recognize each separate center wavelength and variations thereof in the combined transmission of all of the center wavelengths in the reflected signal. This embodiment allows one common lumen 42 and set of fiber optic cables 50 housed therein to monitor the degree of flexure in all joints contained in the probe assembly. In this case the optical source 112 will generate multiple distinct wavelengths and the processor 18 extract changes in signal from each of those wavelengths to compute each of the respective angles in each of the respective joints 38.

A further embodiment is shown in FIG. 14, wherein like numerals with a prefix 1 refer to similar elements to those contained in the preceding figures. A flexible joint 138 of the probe assembly contains a glass strand 156 of the optical fiber, which is bonded at position 200 to an interior wall 146 of the lumen 142. The glass strand 156 consists of a core region 204 surrounded by a cladding region 202, which is well known in the art. A long period grating (LPG) 208 is contained in the core region 204 of the optical fiber, wherein a longitudinal axis of the grating is offset radially from a neutral axis 206 of the glass strand 156.

This offset configuration permits changes in the bend angle of the single glass strand 156, due to flexure of the joint 138, to be determined from corresponding changes in the transmission spectrum of the optical signals in the LPG 208. This single fiber bend sensor, including of the LPG 208 contained in the core 204 of the glass strand 156, can be connected to the flexible joint 138 in a similar manner as described in the above mentioned multiple fiber bundles. Operation of this single fiber bend sensor is also similar to that as described above, wherein excitation optical signals are transmitted along the glass strand 156 from an optical source.

It should be noted that fiber optic LPG's 208 have differing optical characteristics, compared to standard Fiber Bragg Gratings. In a standard Fiber Bragg Grating, the guided optical signals, or light, traveling in the core of the fiber is converted into light traveling backwards in the core in a narrow range of wavelengths (i.e. reflected), after the light has encountered the Bragg Grating. The remaining forward propagating portion of the optical signals transmitted as a guided mode in the core. In contrast, when the optical signals encounter the LPG 208, a portion of the forward propagating optical signal travelling in the core 204, is directed out of the core 204 and converted into forward propagating claddings modes located in the cladding 202. Again, the remaining optical signal is transmitted as a forward propagating guided mode in the core 204.

The core 204 of the glass strand 156, containing the LPG 208 radially offset from the neutral axis 206, is positioned in the flexible joint 138 to provide variation in the transmission spectrum of the LPG 208 of the remaining optical signal, as it is transmitted as a guided mode in the core 204. These variations can be correlated with changes in bend angle of the joint 138. One difference to that of previous embodiments is that only a single fiber containing the LPG 208 is used to measure bend angles. The glass strand 156, containing the offset LPG 208, can be positioned anywhere in the joint 138. In the case where the longitudinal axis of the LPG 208 is positioned on the longitudinal neutral axis 206 of the glass strand 156, at least three glass strands 156, each containing an LPG 208, would be used to calculate a three dimensional position of the arm, as described in previous embodiments using FBGs 54.

Another difference using LPGs 208 is that the property filter receiving the remaining optical signal in the guided mode is positioned so that it measures variations in a selected property of the transmitted signal after it travels through the LPG 208, as compared to measuring the reflected optical signals when a Fiber Bragg Grating is used. This can be accomplished, for example, by positioning the property filter at the distal end of the glass strand 156, after the optical signals have been transmitted through the LPG 208, or by employing a second fiber to bring the remaining transmitted light in the core 204 back to the property filter located at the base of the arm.

The above described probe assembly 12 and associated system components can be employed in wide variety of medical and non-medical applications. Examples of medical applications include surgical procedures, image-guided surgical procedures, diagnostic procedures, and therapeutic procedures. Examples of surgical and image-guided surgical procedures include neurological, orthopedic, and cardiac surgeries, and endoscopic sinosurgical procedures. Examples of diagnostic procedures include computerized tomography, magnetic resonance imaging, xray, fluoroscopy, and ultrasound. Examples of therapeutic procedures include photodynamic therapy, and radiation therapeutic procedures including brachytherapy, radiolabelled antibody therapy, total body irradiation, and intraoperative radiotherapy. Non-medical applications include industrial design, robotics, automated manufacturing, computer-aided design, animation, cinema and movies.

Although the invention has been described with reference to certain specific embodiments, various modifications thereof will be apparent to those skilled in the art without departing from the spirit and scope of the invention as outlined in the claims appended hereto.

The embodiments of the invention in which an exclusive property or privilege is claimed are defined as follows:

1. A probe position sensing system comprising:
an articulated arm including a plurality of sections, a flexible joint extending between and connecting adjacent sections, and at least one sensor assembly extending into said joint and positioned to be subjected to a degree of flexure due to relative displacement of said sections, wherein flexure in said sensor assembly induces a variation in a physical property associated with said sensor assembly, and said variation in said physical property is used to derive an angle between adjacent sections.

2. A probe position sensing system according to claim 1, wherein said at least one sensor assembly is bonded to a surface of said arm.

3. A probe position sensing system according to claim 1, wherein said at least one sensor assembly is comprised of an optical fiber.

4. A probe position sensing system according to claim 3, wherein said optical fiber contains at least one Fiber Bragg Grating situated in a portion of each of said sensor assembly, at least a portion of said Fiber Bragg Grating being located in said flexible joints to be flexed upon relative displacement between said sections.

5. A probe position sensing system according to claim 1, wherein said arm further includes a first joint and a second joint, said first joint having a first sensor assembly associated therewith and said second joint having a second sensor assembly associated therewith, wherein each of said sensor assemblies monitors its respective joint for a corresponding variation in said physical property thereof.

6. A probe position sensing system according to claim 5, wherein said first assembly terminates at said first joint and said second assembly terminates at said second joint.

7. A probe position sensing system according to claim 5, wherein a sensor assembly extends between said plurality of flexible joints, wherein said common assemblies contain at least two corresponding distinct sets of Fiber Bragg Gratings reflecting different center wavelengths, respective ones of said Fiber Bragg Gratings being located at each of said joints.

8. A probe position sensing system according to claim 1, further comprising an instrument to monitor a physical property associated with said sensor assembly.

9. A probe position sensing system according to claim 3, further comprising a light source for propagating light to said optical fiber.

10. A probe position sensing system according to claim 9, wherein variation in at least one property of light propagated in said optical fiber is used to indicate the degree of flexure within said fibers.

11. A probe position sensing system according to claim 4, wherein a plurality of optical fibers extend through said flexible joint.

12. A probe position sensing system according to claim 11, wherein said optical fibers are spaced about a neutral axis of said flexible joint.

13. A probe position sensing system according to claim 12, wherein said plurality of optical fibers are located in a conduit and secured to a wall of said conduit.

14. A probe position sensing system according to claim 11, wherein at least three optical fibers are provided.

15. A probe position sensing system according to claim 1, further comprising at least one medical instrument attached to a distal end of one of said sections.

16. A probe position sensing system according to claim 1, further comprising at least one non-medical instrument attached to a distal end of one of said sections.

17. A probe position sensing system according to claim 5, wherein said sensor assemblies are comprised of an optical fiber.

18. A probe position sensing system according to claim 17, wherein said optical fibers contain a Fiber Bragg Grating positioned proximate to each of said joints.

19. A probe position sensing system according to claim 18, wherein said first sensor assembly terminates at said first joint and said second sensor assembly terminates at said second joint.

20. A probe position sensing system according to claim 8, wherein said instrument derives an angle between adjacent sections from variations in said physical property.

21. A probe position sensing system according to claim 8, further comprising a base unit attached to said articulated arm.

22. A probe position sensing system according to claim 21, further comprising a second articulated arm, said instrument monitoring the relative position of said first and second arms.

23. A probe position sensing system according to claim 22, further comprising a signal processor connected to said sensor assembly by at least one cable capable of transferring information between said sensor assembly and said signal processor.

24. A probe position sensing system according to claim 23, wherein said signal processor includes an optical source.

25. A probe position sensing system according to claim 23, wherein said signal processor includes an electrical source.

26. A probe position sensing system according to claim 23, further comprising a computer system to receive information from said signal processor, and associated software to process said information to determine the spatial location of said articulated arm.

27. A probe position sensing system according to claim 26, further comprising a user interface to indicate the position of each of said probe assemblies to a user of said system, wherein said position is calculated from measured angles between said adjacent sections.

28. A probe position sensing system according to claim 1, wherein said at least one sensor assembly extends through said joint.

29. A probe position sensing system according to claim 1, wherein said variation in said physical property is used to derive a compound angle.

30. A probe position sensing system according to claim 29, wherein said compound angle is used to determine the position of the distal end of said articulated arm in three dimensions.

31. An articulated arm comprising: a plurality of sections; a flexible joint extending between and connecting said sections; a sensor assembly passing through said flexible joint and positioned to be subjected to a degree of flexure due to relative displacement of said sections, said sensor assembly having a first longitudinal axis; and a sensor element having a second longitudinal axis and contained in said sensor assembly, said second longitudinal axis in a spaced apart radial relationship with respect to said first longitudinal axis; wherein flexure of said sensor element inducing a variation in a physical property associated with said sensor element, said variation used to derive an angle between adjacent sections.

32. An articulated arm according to claim 31, wherein said sensor assembly is bonded to a surface of said flexible joint.

33. An articulated arm according to claim 31, wherein said sensor assembly is a fiber optic cable.

34. An articulated arm according to claim 33, wherein said variation is in at least one property of light propagated in said fiber optic cable for indicating said degree of flexure in said fiber.

35. An articulated arm according to claim 34, wherein said property of light is wavelength.

36. An articulated arm according to claim 33, wherein said sensor element is comprised of a long period grating is said flexible joint, said long period grating to be flexed upon relative displacement between said sections.

37. A probe position sensing system for determining a spatial location in a coordinate system of a portion of said articulated arm of claim 31, the system including an instrument to monitor said physical property for deriving said angle.

38. A probe position sensing system of claim 37, wherein said articulated arm further comprises a medical instrument attachable to one of said sections.

* * * * *